United States Patent [19]

Günther

[11] Patent Number: 4,691,056
[45] Date of Patent: Sep. 1, 1987

[54] 3-HALOGENOACETONESULFONAMIDES AND A PROCESS FOR THEIR PREPARATION

[75] Inventor: Dieter Günther, Kelkheim, Fed. Rep. of Germany

[73] Assignee: Hoechst Aktiengesellschaft, Fed. Rep. of Germany

[21] Appl. No.: 904,049

[22] Filed: Sep. 4, 1986

[30] Foreign Application Priority Data

Sep. 6, 1985 [DE] Fed. Rep. of Germany ....... 3531788

[51] Int. Cl.$^4$ ........................................... C07C 143/74
[52] U.S. Cl. ................................................... 564/96
[58] Field of Search ........................................ 564/96

[56] References Cited

U.S. PATENT DOCUMENTS 4,448,988  5/1984  Gunther ................................ 564/95

OTHER PUBLICATIONS

Carpanelli et al., "Chemical Abstracts", vol. 103, (1985), 178236q.

Primary Examiner—Anton H. Sutto
Attorney, Agent, or Firm—Connolly and Hutz

[57] ABSTRACT

The invention relates to new 3-halogenoacetonesulfonamides of the formula $X-CH_2-CO-CH_2-SO_2NH_2$ in which X=F, Cl, Br or I, and to the preparation and use thereof. The preparation of the bromine compound according to the invention is effected by reacting acetonesulfonamide with bromine in aqueous solution. The fluorine, chlorine or iodine compound is prepared by reacting the bromine compound with a fluoride, chloride or iodide in an aprotic solvent. The compounds according to the invention can be used for the preparation of azo dyestuffs, plant protection agents, pharmaceuticals and textile auxiliaries.

3 Claims, No Drawings

3-HALOGENOACETONESULFONAMIDES AND A PROCESS FOR THEIR PREPARATION

The present invention relates to novel 3-halogenoacetonesulfonamides of the general formula I

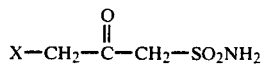

in which X represents F, Cl, Br or I. The invention also relates to a process for the preparation of the compound (I) in which X=Br, which comprises reacting acetonesulfonamide in aqueous solution with bromine. The invention also relates to a process for the preparation of compounds of the formula

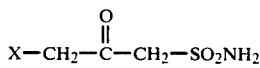

in which X=F, Cl, or I, which comprises reacting 3-bromoacetonesulfonamide in an aprotic solvent in a fluoride, chloride or iodide.

Because of their reactivity, the compounds according to the invention constitute interesting intermediate products, for example for the preparation of azodyestuffs or pigments, plant protection agents, pharmaceuticals or textile auxiliaries.

The bromine compound of the formula (I) is obtained, as mentioned, in a very simple manner by brominating acetonesulfonamide in aqueous solution. Surprisingly, the bromine does not attack the activated carbon atom in the 2-position of the starting compound, as would be expected, nor are any N-bromine derivatives formed.

The fluorine, chlorine or iodine compound of the formula (I) is prepared from the bromine compound by nucleophilic replacement in aprotic dipolar media.

The preparation, according to the invention, of 3-bromoacetonesulfonamide is generally carried out at temperatures from 0° to 100° C. using molar amounts of bromine. It is preferable, however, to select a temperature within the range from 20° to 50° C.

The reaction time depends on the temperature employed and can be detected by the complete decolorization of the reaction mixture.

The acetonesulfonamide employed as the starting material can be obtained as specified in German Offenlegungsschrift 3,323,510 or U.S. Pat. No. 4,448,988. The nucleophilic replacement of the bromine in 3-bromoacetonesulfonamide for the preparation of the three other halogenoacetonesulfonamides of the formula (I) is generally carried out at temperatures between 20° and 100° C. using fluorides, chlorides or iodides in aprotic solvents, such as acetone, dimethylformamide, N-methylpyrrolidone or dimethyl sulfoxide. It is preferable in this reaction to employ fluorides, chlorides or iodides of alkali or alkaline earth metals or of iron, aluminum or zinc. In general, about 1 to 5 mol of halide are used per mole of 3-bromoacetonesulfonamide.

The halogen compounds according to the invention are new, reactive substances which are suitable for use as intermediate products for plant protection agents, pharmaceuticals or textile auxiliaries, and undergo numerous further reactions. For example, their reaction with 2-amino-N-heterocyclic compounds, such as, for example, 2-aminopyridine, provides access to bicyclic compounds which are substituted by sulfonamide groups, such as imidazo[1,2-a]pyridine. It is known that derivatives of such imidazo[1,2-a]pyridines possess a pharmacological action (J.Med.Chem. (1969), 122–26; Eur.J.Med.-Chim. Therapeut. 13, 271-76 (1978)).

However, since the compounds according to the invention, of the formula (I), are also analogs of acetoacetamides, they can—for example after nucleophilic replacement of the halogen atom—be employed as coupling components for the preparation of azo dyestuffs or pigments. The following test report illustrates the synthesis of such an azo pigment:

Test report 6.9 g (50 mmol) of 4-nitroaniline were dissolved in a mixture of 12 ml of concentrated hydrochloric acid and 12 ml of water and cooled to 0° C. 14 ml (53.3 mmol) of 20% strength by weight sodium nitrite solution were added to the solution, and the mixture was stirred for a further 15 minutes at 0° C. The excess sodium nitrite was then destroyed by means of sulfonic acid. The diazonium salt solution was added dropwise at 5° C. to a dispersion of 11.6 g (50 mmol) of bromoacetonesulfonamide in 50 ml of water, the pH being kept meanwhile below 6. After 6 hours the precipitated product was filtered off with suction and dried. 8 g of a yellow dyestuff of the formula

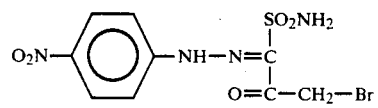

were obtained. The advantage of this azo dyestuff lies in the fact that the activated halogen atom can be replaced by nucleophilic groups and the properties of the dyestuff can thus be modified in a desired manner, and that the acid sulfonamide group can be made into a lake by means of salts, for example salts of barium, calcium or aluminum, as a result of which the solubility of the dyestuffs is greatly reduced, which is very desirable for their use as pigments.

The fluorine, chlorine or iodine compound according to formula (I) can be reacted analogously to the bromine compound to give an azo pigment.

The following examples illustrate the preparation of the compounds according to the invention:

EXAMPLE 1

137.2 g (1 mol) of acetonesulfonamide were suspended in 200 ml of water, and 160 g (1 mol=52 ml) of bromine were added dropwise at 20° C., with cooling (time required approx. 30 minutes). The mixture was stirred for a further hour at room temperature. The solvent was distilled off under a water pump vacuum in a rotary evaporator. The residue obtained was then recrystallized from 1.5 liters of isopropanol. This gave 186 g (86% of theory) of 3-bromoacetonesulfonamide of melting point 119°-120° C.

Elementary analysis: $C_3H_6BrNO_3S$ (molecular weight 216.05): Calculated: C: 16.7; H: 2.8; Br: 37.0; N: 6.5; S: 14.8; Found: C: 17.0; H: 2.7; Br: 37.4; N, 6.5; S: 15.2

NMR spectrum: 100 MHz—$^1$HNMR (DMSO-$d_6$) (ppm): 4.4(2H, s, $\underline{CH_2}$), 4.5(2H, s, $\underline{CH_2}$), 7.2(2H, s, $\underline{NH_2}$).

EXAMPLE 2

137.2 g (1 mol) of acetonesulfonamide in 200 ml of water were heated to 40° C., and 1 mol of bromine was added at this temperature in the course of 2 hours. The mixture was stirred for a further 0.5 hour and worked up as in Example 1. Yield: 181.6 g (84% of theory), melting point: 117°–119° C.

EXAMPLE 3

43.2 g (0.2 mol) of 3-bromoacetonesulfonamide were dissolved in 300 ml of acetone, and 33.2 g (0.2 mol) of potassium iodide were added. After stirring for 5 hours at room temperature, the mixture was filtered with suction and the residue was rinsed with acetone. The mother liquor was evaporated under a water pump vacuum and the residue was recrystallized from 500 ml of isopropanol. 45 g (85% of theory) of 3-iodoacetonesulfonamide of melting point 125°–127° C. were obtained.

Elementary analysis: $C_3H_6INO_3S$ (molecular weight 263.05); Calculated: C: 13.7; H: 2.3; I: 48.2; N: 5.3; S: 12.2; Found: C: 13.7; H: 2.2; I: 48.0; N: 5.6; S: 12.4

NMR spectrum: 100 MHz—$^1$HNMR (DMSO-$d_6$) (ppm): 4.2(2H, s, $\underline{CH_2}$), 4.4(2H, s, $\underline{CH_2}$), 7.2(2H, s, $\underline{NH_2}$).

EXAMPLE 4

4.3 g (20 mmol) of 3-bromoacetonesulfonamide were dissolved in 30 ml of acetone, and 3 g (40 mmol) of potassium chloride were added. The mixture was stirred for 1.5 hours at room temperature and was filtered, and the residue was washed with acetone. The mother liquor was evaporated in a rotary evaporator. The residue was recrystallized from 30 ml of isopropanol to give 3 g of product of melting point 110°–112° C. This was recrystallized again from 30 ml of ethanol, 2.0 g of 3-chloroacetonesulfonamide of melting point 114°–115° C. being obtained.

NMR spectrum: 100 MHz—$^1$HNMR (DMSO-$d_6$) (ppm): 4.3(2H, s, $\underline{CH_2}$), 4.7(2H, s, $\underline{CH_2}$), 7.2(2H, s, $\underline{NH_2}$).

I claim:

1. A compound of the formula

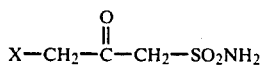

in which X can be fluorine, chlorine, bromine or iodine.

2. A process for the preparation of 3-bromoacetonesulfonamide

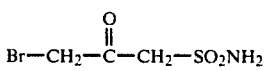

which comprises reacting acetonesulfonamide in aqueous solution with bromine.

3. A process for the preparation of compounds of the formula

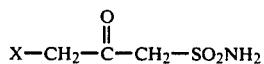

in which X=F, Cl or I, which comprises reacting 3-bromoacetonesulfonamide in an aprotic solvent with fluoride, chloride or iodide.

* * * * *